US007041688B2

(12) United States Patent
Campbell et al.

(10) Patent No.: US 7,041,688 B2
(45) Date of Patent: May 9, 2006

(54) ALKYNLY-SUBSTITUTED SPIROCYCLIC SULFAMIDES FOR THE TREATMENT OF ALZHEIMER'S DISEASE

(75) Inventors: Alister Campbell, London (GB); Mark Peter Ridgill, Watton-at-Stone (GB)

(73) Assignee: Merck Sharp & Dohme Lt.d., Hoddesdon (GB)

( * ) Notice: Subject to any disclaimer, the term of this patent is extended or adjusted under 35 U.S.C. 154(b) by 0 days.

(21) Appl. No.: 10/511,506

(22) PCT Filed: Apr. 24, 2003

(86) PCT No.: PCT/GB03/01771

§ 371 (c)(1), (2), (4) Date: Oct. 15, 2004

(87) PCT Pub. No.: WO03/093253

PCT Pub. Date: Nov. 13, 2003

(65) Prior Publication Data

US 2005/0215602 A1 Sep. 29, 2005

(30) Foreign Application Priority Data

May 1, 2002 (GB) .................................. 0209997

(51) Int. Cl.
*A61K 31/433* (2006.01)
*A61P 25/28* (2006.01)
*C07D 285/14* (2006.01)

(52) U.S. Cl. ................. 514/362; 514/278; 514/255.05; 546/16; 548/126

(58) Field of Classification Search ........... 514/255.05, 514/278, 362; 546/16; 548/126
See application file for complete search history.

(56) References Cited

U.S. PATENT DOCUMENTS

| 3,406,184 A | 10/1968 | Raasch |
| 3,715,362 A | 2/1973 | Dominianni |
| 5,703,129 A | 12/1997 | Felsenstein et al. |

2004/0029862 A1   2/2004   Belanger et al.

FOREIGN PATENT DOCUMENTS

| WO | WO 98/38156 | 9/1998 |
| WO | WO 01/70677 | 9/2001 |
| WO | WO 02/36555 | 5/2002 |

OTHER PUBLICATIONS

J.E. Franz, et al: Journal of Organic Chemistry, vol. 29, No. 10, Oct. 1964, pp. 2922-2927.
R. Huisgen, et al.: Chemische Berichte, vol. 98, No. 12, Dec. 1965, pp. 3992-4013.
S. Itsuno, et al.: Journal of the Chemical Society, Perkin Transactions 1, No. 10, Jul. 15, 1999 pp. 2011-2016.
M. Narisada, et al.: Journal of Medicinal Chemistry, vol. 31, No. 9, Sep. 1988, pp. 1847-1854.
K. B. Sharpless, et al.: Journal of Organic Chemistry, vol. 41, No. 1, Jan. 9, 1976, pp. 176-177.
Y. Yamaguchi, et al.: Xenobiotica, vol. 26, No. 6, Jun. 1996, pp. 613-626.
L. H. Zalkow, et al.: Journal of the American Chemical Society, vo. 86, No. 19, Oct. 5, 1964.
L. H. Zalkow, et al.: Journal of Organic Chemistry, vol. 28, No. 12, Dec. 1963, pp. 3303-3309.
G. M. Rishton et al., "Fenchylamine Sulfonamide Inhibitors of Amyloid Beta Peptide Production by the Gamma-Secretase Proteolytic Pathway . . . ", J. Med. Chem., 2000, 43, 2297-2299.

*Primary Examiner*—Kamal A. Saeed
(74) *Attorney, Agent, or Firm*—John C. Todaro; Melvin Winokur

(57) ABSTRACT

Compounds of formula (I) are disclosed. The compounds inhibit gamma-secretase and hence find use in treatment of Alzheimer's disease

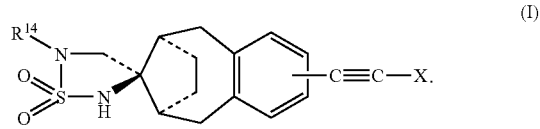

8 Claims, No Drawings

ALKYNLY-SUBSTITUTED SPIROCYCLIC SULFAMIDES FOR THE TREATMENT OF ALZHEIMER'S DISEASE

CROSS REFERENCE TO RELATED APPLICATIONS

This application is a U.S. National Phase application under 35 U.S.C. § 371 of PCT Application No. PCT/GB03/01771, filed Apr. 24, 2003, which claims priority under 35 U.S.C. § 119 from GB Application No. 0209997.6, filed May 1, 2002.

The present invention relates to a novel class of compounds, their salts, pharmaceutical compositions comprising them, processes for making them and their use in therapy of the human body. In particular, the invention relates to compounds which modulate the processing of APP by γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ), and although the exact role of the plaques in the onset and progress of AD is not fully understood, it is generally accepted that suppressing or attenuating the secretion of Aβ is a likely means of alleviating or preventing the condition. (See, for example, ID research alert 1996 1(2): 1–7; ID research alert 1997 2(1):1–8; Current Opinion in CPNS Investigational Drugs 1999 1(3):327–332; and Chemistry in Britain, January 2000, 28–31.)

Aβ is a peptide comprising 39–43 amino acid residues, formed by proteolysis of the much larger amyloid precursor protein. The amyloid precursor protein (APP or AβPP) has a receptor-like structure with a large ectodomain, a membrane spanning region and a short cytoplasmic tail. Different isoforms of APP result from the alternative splicing of three exons in a single gene and have 695, 751 and 770 amino acids respectively.

The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate the soluble, COOH-truncated forms of APP ($APP_s$). Proteases which release APP and its fragments from the membrane are termed "secretases". Most $APP_s$ is released by a putative α-secretase which cleaves within the Aβ domain (between residues $Lys^{16}$ and $Leu^{17}$) to release α-$APP_s$ and precludes the release of intact Aβ. A minor portion of $APP_s$ is released by a β-secretase, which cleaves near the $NH_2$-terminus of Aβ and produces COOH-terminal fragments (CTFs) which contain the whole Aβ domain. Finding these fragments in the extracellular compartment suggests that another proteolytic activity (γ-secretase) exists under normal conditions which can generate the COOH-terminus of Aβ.

It is believed that γ-secretase itself depends for its activity on the presence of presenilin-1. In a manner that is not fully understood presenilin-1 appears to undergo autocleavage.

There are relatively few reports in the literature of compounds with inhibitory activity towards β- or γ-secretase, as measured in cell-based assays. These are reviewed in the articles referenced above. Many of the relevant compounds are peptides or peptide derivatives.

WO 01/70677 discloses certain sulphonamido-substituted bridged bicycloalkyl derivatives which are useful in the treatment of Alzheimer's disease, but neither discloses nor suggests the compounds of the present invention.

The present invention provides a novel class of non-peptidic compounds which are useful in the treatment or prevention of AD by modulating the processing of APP by the putative γ-secretase, thus arresting the production of Aβ and preventing the formation of insoluble plaques.

According to the invention there is provided a compound of formula I:

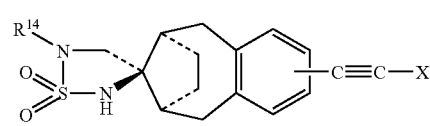

I wherein X represents Ar, $L-N(R^1)_2$, $L-CON(R^1)_2$, $L-CO_2R^1$ or L-CN;

L represents a hydrocarbon chain of 1–7 carbon atoms which, when the chain comprises 2 or more carbon atoms, is optionally interrupted by an oxygen atom;

$R^1$ represents H or $R^2$; or two $R^1$ groups attached to a single nitrogen atom may complete a heterocyclic ring of 3–7 members bearing 0–3 substituents selected from halogen, oxo, $NO_2$, CN, $CF_3$, $R^2$, $C_{2-6}$acyl, $C_{2-6}$alkenyl, OH, $OR^2$, $CO_2H$, $CO_2R^2$, Ar, $ArCH_2O$, and ArO;

$R^2$ represents $C_{1-6}$alkyl which is optionally substituted with halogen, Ar, $NO_2$, CN, $CF_3$, OH or $C_{1-4}$alkoxy;

$R^{14}$ represents H or $C_{1-6}$alkyl, $C_{3-7}$cycloalkyl, $C_{3-6}$cycloalkyl$C_{1-6}$alkyl, $C_{2-6}$alkenyl, $C_{2-6}$alkynyl, phenyl or benzyl, any of which optionally bear up to 3 halogen substituents or one substituent selected from CN, $NO_2$, OH, $C_{1-4}$alkoxy, $CO_2H$, $C_{1-4}$alkoxycarbonyl, $C_{2-6}$acyl, $C_{2-6}$acyloxy, amino, $C_{1-4}$alkylamino, di($C_{1-4}$alkyl)amino, $C_{2-6}$acylamino, carbamoyl, $C_{1-4}$alkylcarbamoyl and di($C_{1-4}$alkyl)carbamoyl; and Ar represents phenyl or heteroaryl either of which optionally bears up to 3 substituents independently selected from halogen, $CF_3$, $NO_2$, CN, $OCF_3$, $C_{1-6}$alkyl and $C_{1-6}$alkoxy;

or a pharmaceutically acceptable salt thereof.

Where a variable occurs more than once in formula I or in a substituent thereof, the individual occurrences of that variable are independent of each other, unless otherwise specified.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner. Most suitably, such groups comprise no more than 4 carbon atoms.

The expression "$C_{3-7}$cycloalkyl" as used herein refers to nonaromatic monocyclic or bicyclic hydrocarbon ring systems comprising from 3 to 7 ring atoms. Examples include cyclopropyl, cyclobutyl, cyclopentyl, cyclohexyl, cyclohexenyl, cycloheptyl and bicyclo[2,2,1]heptyl.

The expression "C$_{3-6}$ cycloalkyl(C$_{1-6}$)alkyl" as used herein includes cyclopropylmethyl, cyclobutylmethyl, cyclopentylmethyl and cyclohexylmethyl.

The expression "C$_{2-6}$acyl" as used herein refers to (C$_{1-5}$alkyl)carbonyl groups, such as acetyl, propanoyl and butanoyl, including cycloalkyl derivatives such as cyclopentanecarbonyl and cyclobutanecarbonyl and halogenated derivatives such as trifluoroacetyl.

The expression "heteroaryl" as used herein means a cyclic or polycyclic system of up to 10 ring atoms selected from C, N, O and S, wherein at least one of the constituent rings is aromatic and comprises at least one ring atom which is other than carbon. Monocyclic systems comprising 5 or 6 ring atoms are preferred. Preferably not more than 3 ring atoms are other than carbon. Where a heteroaryl ring comprises two or more atoms which are not carbon, not more than one of said atoms may be other than nitrogen. Examples of heteroaryl groups include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups and benzo-fused analogues thereof. Further examples of suitable heteroaryl ring systems include 1,2,4-triazine and 1,3,5-triazine.

The term "halogen" as used herein includes fluorine, chlorine, bromine and iodine, of which fluorine and chlorine are preferred.

For use in medicine, the compounds of formula I may advantageously be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

The compounds of formula I exist as two sets of positional isomers, depending on whether the alkynyl group is attached at an ortho position relative to the fused ring junction, or at a meta position relative to said junction. Meta attachment is preferred. For each positional isomer, two enantiomeric forms are possible, depending on which of the two available ortho or two available meta positions is occupied. For each positional isomer, the invention extends to both enantiomers, as pure compounds or as enantiomeric mixtures in any proportion. Furthermore, structural formulae depicting one enantiomeric form are to be construed as representing both enantiomeric forms, unless otherwise stated.

The compounds of formula I are alkynyl-substituted benzo-fused bridged bicycloalkane derivatives comprising a spiro-linked cyclic sulphamide moiety.

In the compounds of formula I, R$^{14}$ preferably represents optionally substituted C$_{1-6}$alkyl (such as methyl, ethyl, n-propyl, isopropyl, n-butyl, t-butyl, sec-butyl, cyanomethyl, 2-fluoroethyl, methoxyethyl, trifluoromethyl and 2,2,2-trifluoroethyl), C$_{3-7}$cycloalkyl (such as cyclopropyl, cyclobutyl, cyclopentyl and cyclohexyl), C$_{3-6}$cycloalkylC$_{1-6}$alkyl (such as cyclopropylmethyl, cyclobutylmethyl and cyclopentylmethyl), C$_{2-6}$alkenyl (such as allyl), C$_{2-6}$alkynyl (such as propargyl), or optionally substituted phenyl or benzyl. R$^{14}$ very aptly represents n-propyl or 2,2,2-trifluoroethyl, an in a particular embodiment R$^{14}$ represents 2,2,2-trifluoroethyl.

In the compounds of formula I, X represents Ar, L-N(R$^1$)$_2$, L-CON(R$^1$)$_2$, L-CO$_2$R$^1$ or L-CN, where Ar, L, R$^1$ and R$^2$ are as defined previously.

In this context, Ar typically represents optionally-substituted phenyl or 6-membered heteroaryl, such as pyridyl, pyrimidinyl or pyrazinyl. Suitable substituents include halogen (especially F or Cl), trifluoromethyl and methyl. In a particular embodiment, X represents 2-pyridyl, 3-pyridyl or pyrazinyl.

The linking group L represents a hydrocarbon chain comprising from 1 to 7 carbon atoms, optionally comprising an oxygen atom in the chain when 2 or more carbon atoms are present. Typically, L comprises from 1 to 6, preferably 1 to 5 carbon atoms. Suitable identities for L include —CH$_2$—, —(CH$_2$)$_4$—, —(CH$_2$)$_5$—, —(CH$_2$)$_2$—O—(CH$_2$)$_2$— and —(CH$_2$)$_2$—O—CH$_2$—.

R$^1$ represents H or R$^2$ where R$^2$ represents C$_{1-6}$alkyl which is optionally substituted with halogen, Ar, NO$_2$, CN, CF$_3$, OH or C$_{1-4}$alkoxy; or two R$^1$ groups attached to a single nitrogen atom may complete a heterocyclic ring of 3–7 members, optionally substituted as defined previously. Examples of groups represented by R$^1$ include H, methyl, ethyl, propyl, butyl, benzyl, hydroxyethyl and methoxyethyl. When two R$^1$ groups combine to form a heterocyclic ring, suitable rings include pyrrolidine, piperidine, tetrahydropyridine, piperazine, morpholine, thiomorpholine and 2,5-diazabicyclo[2,2,1]heptane. Preferred ring substituents include halogen, OH, oxo and R$^2$ groups (such as methyl, ethyl, propyl, hydroxymethyl and methoxymethyl), trifluoromethyl, acetyl, trifluoroacetyl, methoxycarbonyl, phenoxymethyl, pyridyl and phenyl, wherein the pyridyl and phenyl groups optionally bear up to 2 substituents selected from halogen (especially chlorine or fluorine), C$_{1-6}$alkyl and C$_{1-6}$alkoxy. Examples of groups represented by N(R$^1$)$_2$ include benzylamino, N,N-dimethylamino, piperidin-1-yl, morpholin-4-yl, 4-methylpiperazin-1-yl, 4-phenylpiperazin-1-yl, N-(2-methoxyethyl)-N-methylamino, 4-trifluoromethylpiperidin-1-yl, 4,4-difluoropiperidin-1-yl, 5-aza-2-oxabicyclo[2.2.1]hept-5-yl, 1,2,3,6-tetrahydropyridin-1-yl, N-(pyridin-2-ylmethyl)amino, N,N-bis(2-methoxyethyl)amino, 3,3-difluoropyrrolidin-1-yl, 4-hydroxy-4-trifluoromethylpiperidin-1-yl, 3-oxopiperazin-1-yl, 3-oxo-4-phenylpiperazin-1-yl, 4-methylpiperidin-1-yl, N-(2,2,2-trifluoroethyl)amino, N-(thiophene-2-ylmethyl)amino, 2-phenoxymethylmorpholin-4-yl, 3-(pyridin-3-yl)-pyrrolidin-1-yl, N-(4-phenylmorpholin-2-ylmethyl)amino and 3-hydroxypiperidin-1-yl. Particular groups represented by N(R$^1$)$_2$ include benzylamino and 4-trifluoromethylpiperidin-1-yl.

A preferred subclass of the compounds of formula I are in accordance with formula II:

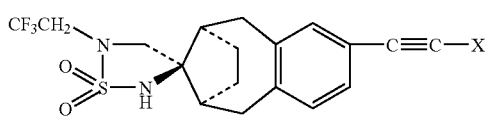

where X is as defined previously.

In one embodiment of this subset, X is selected from 6-membered heteroaryl, —CH$_2$N(R$^1$)$_2$, —(CH$_2$)$_5$N(R$^1$)$_2$, —(CH$_2$)$_4$CON(R$^1$)$_2$, —(CH$_2$)$_4$CO$_2$R$^2$, —(CH$_2$)$_2$—O—CH$_2$CN and —(CH$_2$)$_2$—O—(CH$_2$)$_2$N(R$^1$)$_2$.

Particular compounds in accordance with formula II include those in which X represents 2-pyridyl, 3-pyridyl, pyrazinyl, 4-trifluoropiperidin-1-ylmethyl, —(CH$_2$)$_5$NH—CH$_2$Ph, —(CH$_2$)$_4$CONHCH$_2$Ph, —(CH$_2$)$_4$CO$_2$H, —(CH$_2$)$_2$—O—CH$_2$CN and —(CH$_2$)$_2$—O—(CH$_2$)$_2$NH$_2$.

The compounds of the present invention have an activity as inhibitors of γ secretase.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of the invention or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of the present invention or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to the present invention or a pharmaceutically acceptable salt thereof.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(vinylpyrrolidone) or gelatin.

For treating or preventing Alzheimer's Disease, a suitable dosage level is about 0.01 to 250 mg/kg per day, preferably about 0.01 to 100 mg/kg per day, and especially about 0.01 to 5 mg/kg of body weight per day. The compounds may be administered on a regimen of 1 to 4 times per day. In some cases, however, dosage outside these limits may be used.

The compounds of formula I may be prepared by reaction of triflates III with alkynes HC≡C—X:

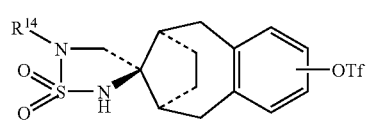

where Tf represents trifluoromethanesulphonyl (triflyl) and X and R$^{14}$ have the same meanings as before. The reaction is typically carried out at elevated temperature (e.g. 90–150° C.) under nitrogen in a sealed container in the presence of (Ph$_3$P)$_4$Pd(0), copper iodide, an amine and a solvent such as dioxan. Microwave heating may be employed.

Alternatively, the triflates III may be reacted with trimethysilylacetylene under similar conditions to provide alkynes IV(a):

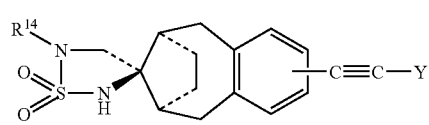

(a) Y = SiMe$_3$
(b) Y = H where R$^{14}$ has the same meaning as before. Hydrolysis of IV(a) (e.g. with LiOH in aqueous THF) provides acetylenes IV(b), which react with compounds X-G, where G is a suitable leaving group such as halogen (especially Br or I)

and X has the same meaning as before, to provide compounds of formula I. The reaction takes place in the presence of (Ph$_3$P)$_4$Pd(0), copper iodide and an amine as before, and this route is particularly suitable when X represents Ar.

Individual compounds in accordance with formula I may be converted to different compounds in accordance with formula I by application of known synthetic techniques. For example, compounds of formula I in which X represents L-CN may be hydrolysed to the corresponding compounds in which X represents L-CO$_2$H, or reduced to the corresponding compounds in which X represents L-CH$_2$NH$_2$. Similarly, compounds of formula I in which X represents L-CO$_2$H may be coupled with R$^2$OH or (R$^1$)$_2$NH to provide the corresponding esters or amides wherein X represents, respectively, L-CO$_2$R$^2$ or L-CON(R$^1$)$_2$. Furthermore, compounds of formula I in which X represents L-CON(R$^1$)$_2$ may be reduced to the corresponding amines in which X represents L-CH$_2$N(R$^1$)$_2$.

Where they are not commercially available, the above-mentioned reagents may be prepared by conventional routes. The synthesis of triflate III in which R$^{14}$ represents 2,2,2-trifluoroethyl is described in the Examples, and analogous routes may be followed for other identities of R$^{14}$.

Where more than one isomer can be obtained from the above-described reaction schemes, then the resulting mixture of isomers can be separated by conventional means.

Where the above-described processes for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

A typical assay which can be used to determine the level of activity of compounds of the present invention is as follows:

(1) Mouse neuroblastoma neuro 2a cells expressing human app695 are cultured at 50–70% confluency in the presence of sterile 10 mM sodium butyrate.
(2) Cells are placed in 96-well plates at 30,000/well/100 μL in minimal essential medium (MEM) (phenol red-free)+ 10% foetal bovine serum (FBS), 50 mM HEPES buffer (pH7.3), 1% glutamine, 0.2 mg/ml G418 antibiotic, 10 mM sodium butyrate.
(3) Make dilutions of the compound plate. Dilute stock solution to 5.5% DMSO/110 μM compound. Mix compounds vigorously and store at 4° C. until use.
(4) Add 10 μL compound/well. Mix plate briefly, and leave for 18 h in 37° C. incubator.
(5) Remove 90 μL of culture supernatant and dilute 1:1 with ice-cold 25 mM HEPES (pH.3), 0.1% BSA, 1.0 mM EDTA (+broad spectrum protease inhibitor cocktail; pre-aliquotted into a 96-well plate). Mix and keep on ice or freeze at −80° C.
(6) Add back 100 μL of warm MEM+10% FBS, 50 mM HEPES (pH7.3), 1% glutamine, 0.2 mg/ml G418, 10 mM sodium butyrate to each well, and return plate to 37° C. incubator.
(7) Prepare reagents necessary to determine amyloid peptide levels, for example by ELISA assay.
(8) To determine if compounds are cytotoxic, cell viability following compound administration is assessed by the use of redox dye reduction. A typical example is a combination of redox dye MTS (Promega) and the electron coupling reagent PES. This mixture is made up according to the manufacturer's instructions and left at room temperature.
(9) Quantitate amyloid beta 40 and 42 peptides using an appropriate volume of diluted culture medium by standard ELISA techniques.
(10) Add 15 μL/well MTS/PES solution to the cells; mix and leave at 37° C.
(11) Read plate when the absorbance values are approximately 1.0 (mix briefly before reading to disperse the reduced formazan product).

Alternative assays are described in *Biochemistry*, 2000, 39(30), 8698–8704.

The Examples of the present invention all had an ED$_{50}$ of less than 100 nM, typically less than 50 nM and in most cases less than 10 nM in at least one of the above assays.

The following examples illustrate the present invention.

EXAMPLES

Intermediate 1

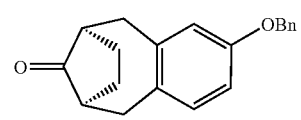

Step 1

A mixture of 2-hydroxy-5,6,7,8,9,10-hexahydro-6,9-methanobenzo[α][8]annulen-11-one (15 g; J. Org. Chem 1982, 47, 4329), K$_2$CO$_3$ (20.5 g) and benzyl bromide (10.6 ml) in DMF (100 ml) was stirred for 48 hrs at room temperature. The reaction was diluted with water (500 ml) and extracted with EtOAc (3×150 ml). The combined organic phases were washed with water (2×300 ml), brine (150 ml), dried and concentrated to give a gummy oil which crystallized on standing and after trituration with ether the title benzyl ether (19.5 g, 90%) as a white solid (360 MHz 1H, δ-CDCl$_3$) 1.32 (2H, m), 1.85 (2H, m), 2.57 (2H, m), 2.87 (4H, m), 5.05 (2H, s), 6.82 (2H, m), 7.11 (1H, d, J=8.2), 7.37 (5H, m).

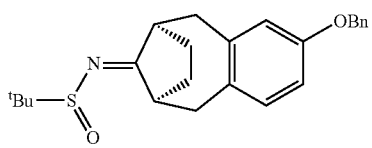

Step 2

A solution of the product from Step 1 (20 g, 68 mmol), (+/−)tert-butyl sulfinamide (9.2 g, 76 mmol) and titanium (IV) ethoxide (tech., 29.2 mL, 140 mmol) in dry THF (140 mL) was stirred and heated at reflux under nitrogen for 4 hours. The reaction was allowed to cool to room temperature and poured into rapidly stirred brine (160 mL). The mixture was stirred for 20 minutes, then filtered through Hyflo®, washing with ethyl acetate. The filtrate was transferred to a separating funnel. The layers were separated, and the aqueous layer was extracted with ethyl acetate (×1). The combined organic extracts were washed with brine, then dried (Na$_2$SO$_4$), filtered and evaporated. The residue was purified by chromatography on silica, eluting with 20→30% ethyl acetate/hexanes, to give the imine (24.9 g, 93%) as a colourless solid. MS(ES+) 396, MH$^+$.

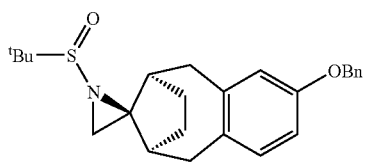

Step 3

Sodium hydride (60% dispersion in oil, 3.8 g, 95 mmol) was added portionwise to a stirred suspension of trimethyl sulfoxonium iodide (21 g, 95 mmol) in dry DMSO (150 mL) at room temperature under nitrogen. After 90 minutes at room temperature, a solution of the product from Step 2 (24.9 g, 95 mmol) in dry DMSO (250 mL) was added such that the internal temperature remained below 30° C. The mixture was stirred at room temperature for 4 hours, then quenched with water (1 L). The precipitate was collected by filtration. The solid was taken up in dichloromethane and washed with brine. The organic layer was dried (Na$_2$SO$_4$), filtered and evaporated. The residue was purified by chromatography on silica, eluting with 5→10% ethyl acetate/dichloromethane, to give the aziridine (23.2 g, 90%) as a colourless solid. MS(ES+) 410, MH$^+$.

Step 4

Trifluoroethyl amine (70 mL, 880 mmol) was added to a stirred suspension of the product from Step 3 (68.4 g, 167 mmol) and anhydrous zinc iodide (54 g, 170 mmol) in dry 1,2-dichloroethane (300 mL) at room temperature under nitrogen. The resulting solution was heated at 75° C., protected from light for 24 hours, an additional portion of trifluoroethyl amine (70 mL, 880 mmol) added and the reaction maintained at 75° C. for a further 16 hours. The reaction was allowed to cool, then diluted with dichloromethane (500 mL) and water (400 mL). Sufficient sodium carbonate was then added to adjust the aqueous layer to ~pH 11. The small amount of precipitate was removed by filtration through Hyflo® The layers were separated and the aqueous layer was extracted with dichloromethane (×3). The combined organic extracts were dried (Na$_2$SO$_4$), filtered and evaporated. The residue was purified by chromatography on silica, eluting with 5→10% ethyl acetate/dichloromethane, then with 10→20% methanol/dichloromethane, to give the diamine (59.6 g, 88%) as a thick oil. MS(ES+) 405, MH$^+$.

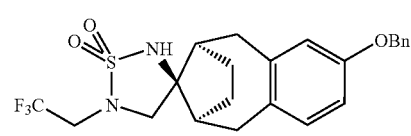

Step 5

A solution of the product from Step 4 (59.6 g, 147 mmol) and sulfamide (42.5 g, 442 mmol) in dry pyridine (350 mL) was stirred and heated at reflux under nitrogen for 4 hours. The reaction was allowed to cool, then the pyridine was removed in vacuo. The residue was azeotroped with toluene (×2) and the residue partitioned between dichloromethane (400 mL) and 1N hydrochloric acid (400 mL). The layers were separated and the aqueous layer was extracted with dichloromethane (3). The combined organic extracts were dried (Na$_2$SO$_4$), filtered and evaporated. The residue was purified by chromatography on silica, eluting with dichloromethane, then 1→2→4% ethyl acetate/dichloromethane to give the cyclic sulfamide (53 g, 80%) as a colourless solid. $^1$H NMR (360 MHz, CDCl$_3$) δ$_H$ 1.34 (2H, m), 1.70 (2H, m), 2.41 (2H, m), 2.62 (2H, m), 3.11 (2H d, J=15.9), 3.20 (1H, d, J=15.9), 3.42 (2H, ABq, J=9.3, 13.3), 3.67 (2H, dq, J=2.2, 8.7), 4.76 (1H, s), 5.02 (2H, s), 6.72 (2H, m), 6.99 (1H, d, J=7.8), 737 (5H, m).

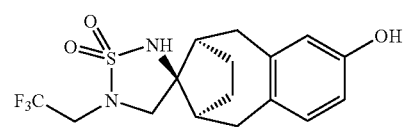

Step 6

A solution of the product from Step 5 (3.9 g, 8.4 mmol) in methanol/ethyl acetate (4:1, 150 mL) was hydrogenated at 35 psi over 10% palladium on carbon (500 mg) for 4 hours at room temperature. The catalyst was removed by filtration through Hyflo®. The filtrate was evaporated, and the residue was purified by filtration through a pad of silica, eluting with 50% ethyl acetate/dichloromethane to give the phenol (3.2 g) colourless solid. $^1$H NMR (360 MHz, d$_6$-DMSO) δ$_H$ 1.06 (2H, m), 1.65 (2H, m), 2.29 (2H, m), 2.42 (2H, m), 3.04 (1H, d, J=15.6), 3.11 (1H, d, J=15.6), 3.43 (2H, s), 3.99 (2H, brq, J=9.6), 6.47 (2H, m), 6.85 (1H, d, J=8), 7.93 (1H, s), 9.02 (1H, s).

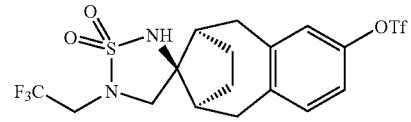

Step 7

Pyridine (2.1 mL, 26 mmol) was added dropwise to a stirred solution/suspension of the product from Step 6 (7.7 g, 20 mmol) and triflic anhydride (4.3 mL, 25.6 mmol) in dry dichloromethane (200 mL) at 0° C. under nitrogen. The cooling bath was removed and the reaction was stirred at room temperature for 4 hours. Water (300 mL) was added and the layers were separated. The aqueous layer was extracted with dichloromethane (×2). The combined extracts were washed with brine (×1), then dried ($Na_2SO_4$), filtered and evaporated. The residue was purified by chromatography on silica, eluting with 5% ethyl acetate/dichloromethane, to give the triflate (6.7 g, 65%) as an off white solid. $^1$H NMR (360 MHz, $d_6$-DMSO) $\delta_H$ 0.99 (2H, m), 1.71 (2H, m), 2.38 (2H, brm), 2.69 (2H, m), 3.16 (1H, d, J=15.7), 3.18 (1H, d, J=15.7), 3.46 (2H, s), 4.02 (2H, brq, J=9.6), 7.18–7.31 (3H, m), 8.04 (1H, s).

Example 1

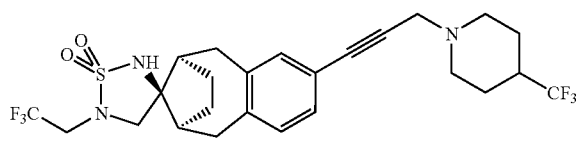

Step 1

4-Trifluoromethylpiperidine (2.0 g, 13 mmol) was added to a solution of propargyl bromide (80 wt. % 5.4 g, 36 mmol) in ethanol (30 ml). Potassium carbonate (5.4 g, 39 mmol) was added and the mixture was stirred at room temperature for 20 hours. The mixture was filtered and the solids washed with ethyl acetate. The filtrate was evaporated in vacuo, diluted with sodium hydrogen carbonate (sat, 50 ml) and extracted with ethyl acetate (2×40 ml). The extracts were washed with brine, dried ($MgSO_4$) and evaporated in vacuo to provide 1-propargyl-4-trifluoromethylpiperidine as a brown oil (795 mg, 32%). (ES+) 192 ([MH]$^+$).

Step 2

A mixture of Intermediate 1 (200 mg, 0.39 mmol), the product from Step 1 (148 mg, 0.78 mmol), tetrakis-triphenylphospine palladium(0) (23 mg, 5 mol %), triphenyl phosphine (10 mg, 10 mol %) and copper iodide (7.6 mg, 10 mol %) in piperidine (2 ml), in a crimp-top microwave vial, was sealed, purged with nitrogen and then irradiated in the Smith Synthesizer Microwave to 150° C. for 15 minutes. The reaction was diluted with sodium hydrogen carbonate (sat, 25 ml) and extracted with ethyl acetate (2×25 ml). The extracts were washed with water (10 ml) and brine, dried ($MgSO_4$) and evaporated in vacuo to a brown gum, which was purified by flash column chromatography on silica eluting with 20 to 30% EtOAc in isohexane to give a beige gum. The gum was further purified by preparative TLC on silica eluting with 20% EtOAc in isohexane to give the title compound as a white solid (42 mg, 20%). δ ($^1$H, 400 MHz, $CDCl_3$) 1.24–1.35 (2H, m), 1.64–1.75 (4H, m), 1.88–1.92 (2H, m), 1.99–2.08 (1H, m), 2.25 (2H, dd, J=11.7 & 2.1 Hz), 2.42–2.46 (2H, m), 2.57–2.72 (2H, m), 3.03–3.06 (2H, m), 3.18 (2H, dd, J=16.0 & 7.4 Hz), 3.43 (2 h, s), 3.52 (2H, s), 3.64–3.70 (2H, m), 4.68 (1H, brs), 7.03 (1H, d, J=7.8 Hz) and 7.18–7.20 (2H, m). (ES+) 550 ([MH]$^+$).

Example 2

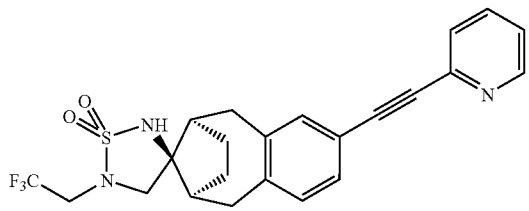

Step 1

A solution of Intermediate 1 (200 mg, 0.39 mmol), trimethylsilylacetylene (112 μl, 0.78 mmol), tetrakis-triphenylphospine palladium(0) (20 mg, 5 mol %), triphenyl phosphine (10 mg, 10 mol %) and copper iodide (7.6 mg, 1 mol %) was made up in 2 ml of dry piperidine and added to a crimp top microwave vial. The vial was sealed, purged with nitrogen and then irradiated in the Smith Synthesizer Microwave to 150° C. for 10 minutes. The reaction was diluted with EtOAc (100 ml) and the mixture washed successively with dilute $NaHCO_3$, 1M HCl solution and then saturated brine solution. The organic layer was then separated, dried ($MgSO_4$) and evaporated in vacuo giving a crude residue which was purified by flash column chromatography using 25% EtOAc in isohexane as eluant to give the trimethylsilylethynyl derivative as a white solid (156 mg, 86% yield). δ ($^1$H, 400 MHz, $CDCl_3$) 0.23 (9H, s), 1.25–1.30 (2H, m), 1.68–1.72 (2H, m), 2.42–2.45 (2H, m), 2.62–2.71 (2H, m), 3.15–3.22 (2H, m), 3.42 (2H, s), 3.67 (2H, q, J=8.7 Hz), 4.68 (1H, brs), 7.03 (1H, d, J=8.2 Hz) and 7.22–7.24 (2H, m).

Step 2

A solution of the product of Step 1 (156 mg, 0.34 mmol) in a 10:1 tetrahydrofuran/water mixture (10 ml) was treated with lithium hydroxide (41 mg, 1.71 mmol) and stirred at room temperature for 1.5 hours. The reaction mixture was diluted with 50 ml dichloromethane and washed with saturated brine solution. The organic phase was dried ($MgSO_4$) and evaporated to dryness before purification by flash column chromatography using 20% ethyl acetate in isohexane as eluant to give the ethynyl derivative as a colourless film (86 mg, 66%). δ ($^1$H, 400 MHz, $CDCl_3$) 1.28–1.32 (2H, m), 1.68–1.72 (2H, m), 2.42–2.46 (2H, m), 2.62–2.71 (2H, m), 3.05 (1H, s), 3.15–3.22 (2H, m), 3.43 (2H, s), 3.67 (2H, q, J=8.7 Hz), 4.66 (1H, brs), 7.03 (1H, d, J=8.2 Hz) and 7.22–7.24 (2H, m).

Step 3

A mixture of the acetylene derivative from Step 2 (32.5 mg, 0.085 mmol), 2-bromopyridine (20 mg, 0.127 mmol), tetrakis-triphenylphospine palladium(0) (8 mg, 10 mol %), triphenyl phosphine (2 mg, 10 mol %) and copper iodide (1.7 mg, 10 mol %) in dry piperidine (2 ml) was added to a crimp top microwave vial, which was then sealed, purged with nitrogen and irradiated in the Smith Synthesizer Microwave to 140° C. for 10 minutes. After this time the reaction was diluted with EtOAc (30 ml) and the mixture washed successively with dilute $NaHCO_3$, 1M HCl solution and then saturated brine solution. The organic layer was separated, dried ($MgSO_4$) and evaporated in vacuo, giving a crude residue which was taken up in 1 ml DMSO and purified by mass directed HPLC. δ ($^1$H, 400 MHz, $CDCl_3$) 1.26–1.35 (2H, m), 1.71–1.75 (2H, m), 2.47 (2H, m), 2.65–2.75 (2H, m), 3.12–3.22 (2H, dd), 3.43 (2H,s), 3.65–3.71 (2H, q), 4.8 (1H, brs), 7.1 (1H, m), 7.37–7.40 (2H, m), 7.42–7.47 (1H, m), 7.59–7.62 (1H, m), 7.88–7.93 (1H, m), 8.72 (1H, m). (ES+) 462 ([MH]⁺).

Example 3

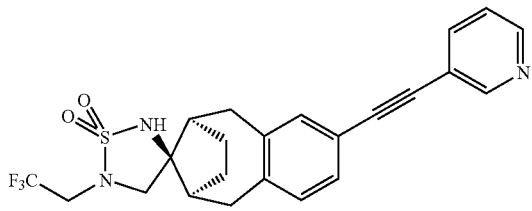

Prepared as in Example 2, using 3-bromopyridine in Step 3. δ (¹H, 400 MHz, CDCl₃) 1.26–1.35 (2H, m), 1.71–1.75 (2H, m), 2.47 (2H, m), 2.65–2.75 (2H, m), 3.12–3.22 (2H, dd), 3.43 (2H,s), 3.65–3.71 (2H, q), 4.68 (1H, brs), 7.1 (1H, m), 7.31–7.33 (2H, m), 7.48–7.51 (1H, m), 7.90–8.02 (1H, m), 8.60–8.62 (1H, m), 8.82 (1H, s). (ES+) 462 ([MH]⁺).

Example 4

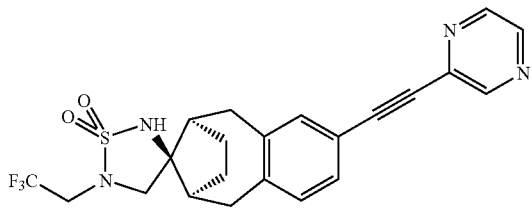

Prepared as in Example 2, using iodopyrazine in Step 3. δ (¹H, 400 MHz, CDCl₃) 1.31–1.34 (2H, m), 1.72–1.76 (2H, m), 2.46–2.49 (2H, m), 2.68–2.77 (2H, m), 3.21–3.27 (2H, dd), 3.44 (2H, s), 3.65–3.71 (2H, q), 4.71 (1H, brs), 7.12–7.14 (1H, d), 7.38–7.39 (2H, m), 8.48 (1H, d), 8.57 (1H, m), 8.74 (1H, s). (ES+) 463 ([MH]⁺).

Example 5

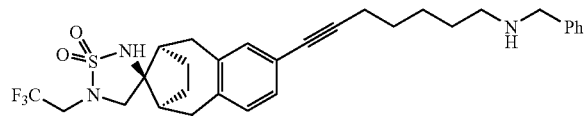

Step 1

1-(3-dimethylaminopropyl)-3-ethylcarbodiimide (3.3 g, 17.4 mmol) was added to a mixture of 6-heptynoic acid (1.1 g, 8.7 mmol), benzylamine (950 μl, 8.7 mmol), 1-hydroxybenzotriazole (1.2 g, 8.7 mmol) and triethylamine (2.4 ml, 17.4 mmol) in tetrahydrofuran (25 ml) and the mixture was stirred at room temperature for 16 hours. The reaction was diluted with sodium hydrogen carbonate (sat, 60 ml) and extracted with ethyl acetate (2×100 ml). The extracts were washed with brine, dried (MgSO₄) and evaporated in vacuo to provide 6-heptynoic acid N-benzylamide as a brown solid (2.1 g, 99%). (ES+) 216 ([MH]⁺).

Step 2

Lithium aluminium hydride (1 m in THF, 10 ml, 10 mmol) was added to a solution of the amide from Step 1 (1.0 g, 4.6 mmol) in THF (20 ml) and the mixture was heated at reflux for 16 hours. The reaction was cooled in ice and treated successively with water (0.4 ml), sodium hydroxide (0.4 ml) and water (1.2 ml) allowing 10 minutes between additions. The mixture was filtered through a bed of Celite® and washed through with THF. The filtrate was evaporated in vacuo to provide 7-(N-benzylamino)hept-1-yne as a yellow oil (924 mg, 99%). (ES+) 202 ([MH]⁺).

Step 3

A mixture of Intermediate 1 (300 mg, 0.6 mmol), the alkyne from Step 2) (482 mg, 2.4 mmol), tetrakis-triphenylphospine palladium(0) (35 mg, 5 mol %), triphenyl phosphine (16 mg, 10 mol %) and copper iodide (12 mg, 10 mol %) in triethylamine (5 ml) in a sealed tube was purged with nitrogen and then heated at 90° C. for 16 hours. The reaction was diluted with sodium hydrogen carbonate (sat, 30 ml) and extracted with ethyl acetate (2×20 ml). The extracts were washed with water (×3) and brine, dried (MgSO₄) and evaporated in vacuo to a dark oil, which was purified by flash column chromatography on silica eluting with DCM:MeOH:NH₃(aq) (120:8:1) to give a brown gum. The gum was further purified flash column chromatography on silica eluting with EtOAc in isohexane (50%+1% NH₃ (aq)) to give the title compound as a clear foam (241 mg, 72%). δ (¹H, 400 MHz, CDCl₃) 1.28–1.32 (2H, m), 1.45–1.71(8H, m), 2.38–2.44 (4H, m), 2.60–2.70 (4H, m), 3.16 (2H, dd, J=16.0 & 10.1 Hz), 3.42 (2H, s), 3.67 (2H, q, J=8.6 Hz), 3.79 (2H, s), 7.00 (1H, d, J=7.8 Hz), 7.13–7.16 (2H, m), and 7.22–7.32 (4H, m). (ES+) 560 ([MH]⁺).

Example 6

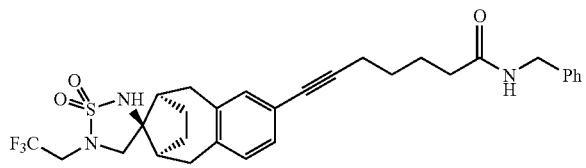

Step 1

A mixture of Intermediate 1, (150 mg, 0.3 mmol), the amide from Example 5, Step 1 (258 mg, 1.2 mmol), tetrakis-triphenylphospine palladium(0) (17 mg, 5 mol %), triphenyl phosphine (8.6 mg, 10 mol %) and copper iodide (6 mg, 10 mol %) in triethylamine (4 ml) in a sealed tube, was purged with nitrogen and then heated at 100° C. for 16 hours. Dioxane (4 ml) and tetrakis-triphenylphospine palladium(0) (17 mg, 5 mol %), triphenyl phosphine (8.6 mg, 10 mol %) and copper iodide (6 mg, 10 mol %) were added and the reaction was heated at 100° C. for 16 hours. The reaction was diluted with sodium hydrogen carbonate (sat, 30 ml) and extracted with ethyl acetate (2×20 ml). The extracts were washed with water (×3) and brine, dried (MgSO₄) and evaporated in vacuo to a brown gum, which was purified by flash column chromatography on silica eluting with EtOAc: isohexane (3:2) to give a beige foam (79 mg, 46%). δ (¹H, 400 MHz, CDCl₃) 1.24–1.32 (2H, m), 1.63–1.72 (4H, m), 1.83–1.87 (2H, m), 2.27 (2H, t, J=7.6 Hz), 2.43 (2H, t, J=), 2.60–2.70 (2H, m), 3.17 (2H, dd, J= 16.0 & 11.4 Hz), 3.42 (2H, s), 3.67 (2H, q, J=8.7 Hz), 4.45 (2H, d, J=5.7 Hz), 4.70

(1H, Brs), 5.70 (1H, Brs), 6.99 (1H, d, J=8.2 Hz), 7.13–7.14 (2H, m), and 7.27–7.33 (5H, m). (ES+) 574 ([MH]+).

Example 7

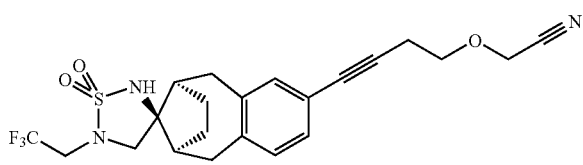

Step 1

A solution of 3-butyn-1-ol (5.0 ml, 77 mmol) in THF (20 ml) was added to a suspension of hexane-washed sodium hydride (3.7 g, 92.5 mmol) in THF (50 ml), under a nitrogen atmosphere at 0° C. The reaction was stirred at 0° C. for 90 minutes before a solution of chloroacetonitrile (5.9 ml, 92.5 mmol) in THF (20 ml) was added dropwise. The black solution was stirred at 0° C. for 15 minutes and at room temperature for 16 hours. The reaction was quenched by the careful addition of brine (150 ml) and the mixture was concentrated in vacuo. The residue was extracted with DCM (3×100 ml). The extracts were dried (MgSO$_4$) and evaporated in vacuo to a dark oil, which was purified by flash column chromatography on silica eluting with EtOAc:isohexane (1:9) to give 3-butyn-1-yloxyacetonitrile as a yellow liquid (777 mg, 9%). (ES+) 110 ([MH]+).

Step 2

A mixture of Intermediate 1 (508 mg, 1.0 mmol), the alkyne from Step 1 (218 mg, 2.0 mmol), tetrakis-triphenylphospine palladium(0) (58 mg, 5 mol %), triphenyl phosphine (26 mg, 10 mol %) and copper iodide (20 mg, 10 mol %) in triethylamine (2 ml) and dioxane (2 ml) in a sealed tube, was purged with nitrogen and then heated at 100° C. for 16 hours. The reaction was diluted with sodium hydrogen carbonate (sat, 20 ml) and extracted with ethyl acetate (2×20 ml). The extracts were washed with water (2×20 ml) and brine, dried (MgSO$_4$) and evaporated in vacuo to a brown gum, which was purified by flash column chromatography on silica eluting with EtOAc:isohexane (20 to 25 to 30%) to give a pale foam (354 mg, 76%). δ ($^1$H, 400 MHz, CDCl$_3$) 1.24–1.32 (2H, m), 1.68–1.72 (2H, m), 2.43 (2H, t, J=7.0 Hz), 2.60–2.76 (4H, m), 3.18 (2H, dd, J=16.0 & 8.2 Hz), 3.64–3.70 (2H, m), 3.79 (2H, t, J=6.7 Hz), 4.33 (2H, s), 4.68 (1H, Brs), 7.00 (1H, d, J=8.2 Hz), and 7.16–7.18 (2H, m). (ES+) 468 ([MH]+).

Example 8

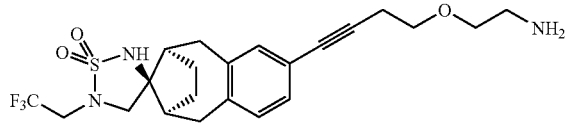

Lithium aluminium hydride (1M in THF, 0.71 ml, 0.71 mmol) was added to a cold (0° C.) solution of the nitrile from Example 7 Step 2 (330 mg, 0.71 mmol) in THF (10 ml) and the mixture was stirred at 0° C. for 2 hours. The reaction was treated successively with water (28 μl), sodium hydroxide (28 μl) and water (84 μl) allowing 10 minutes between additions. The mixture was filtered through a bed of Celite® and washed through with THF. The filtrate was evaporated in vacuo to a gummy solid which was purified by SCX ion exchange resin eluting with ammonia (2M in methanol) to give after evaporation a pale yellow gum (195 mg, 58%). δ ($^1$H, 400 MHz, CDCl$_3$) 1.25–1.34 (2H, m), 1.67–1.71 (2H, m), 2.41–2.44 (2H, m), 2.60–2.71 (4H, m), 2.84–2.90 (2H, m), 3.17 (2H, dd, J=16.0 & 8.2 Hz), 3.42 (2H, s), 3.48–3.50 (2H, m), 3.49–3.70 (4H, m), 7.00 (1H, d, J=8.2 Hz), and 7.15–7.17 (2H, m).

(ES+) 472 ([MH]+).

Example 9

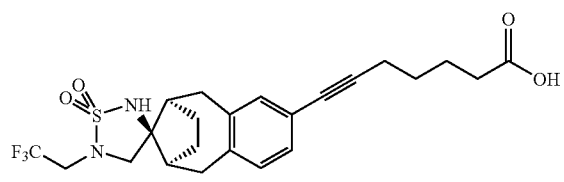

A mixture of Intermediate 1 (100 mg, 0.2 mmol), 6-heptynoic (101 μl, 0.8 mmol), tetrakis-triphenylphospine palladium(0) (12 mg, 5 mol %), triphenyl phosphine (5.2 mg, 10 mol %) and copper iodide (4 mg, 10 mol %) in triethylamine (2 ml) and dioxane (2 ml) was purged with nitrogen and then heated at 100° C. for 16 hours. The reaction was diluted with hydrochloric acid (1N) and extracted with ethyl acetate (2×25 ml). The extracts were washed with water (×3) and brine, dried (MgSO$_4$) and evaporated in vacuo to a yellow gum, which was purified by flash column chromatography on silica eluting with EtOAc:isohexane (1:3) to give a foam which was further purified by preparative TLC eluting with EtOAc:isohexane (1:3) to give a clear gum (11 mg, 12%). δ ($^1$H, 400 MHz, CDCl$_3$) 1.25–1.34 (2H, m), 1.57–1.84 (6H, m), 2.32–2.46 (8H, m), 2.55–2.69 (2H, m), 3.18 (2H, dd, J=16.0 & 9.7 Hz), 3.42 (2H, s), 3.67 (2H, q, J=8.7 Hz), 7.00 (1H, d, J=8.2 Hz), and 7.14–7.16 (2H, m).

(ES+) 483 ([MH]−).

The invention claimed is:

1. A compound of formula I:

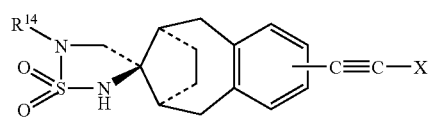

wherein X represents Ar, L-N($R^1$)$_2$, L-CON($R^1$)$_2$, L-CO$_2$$R^1$ or L-CN;

L represents a hydrocarbon chain of 1–7 carbon atoms which, when the chain consists of 2 or more carbon atoms, is optionally interrupted by an oxygen atom;

$R^1$ represents H or $R^2$; or two $R^1$ groups attached to a single nitrogen atom may complete a heterocyclic ring of 3–7 members bearing 0–3 substituents selected from halogen, oxo, $NO_2$, CN, $CF_3$, $R^2$, $C_{2-6}$acyl, $C_{2-6}$alkenyl, OH, $OR^2$, $CO_2H$, $CO_2R^2$, Ar, $ArCH_2O$, and ArO;

$R^2$ represents $C_{1-6}$alkyl which is optionally substituted with halogen, Ar, $NO_2$, CN, $CF_3$, OH or $C_{1-4}$alkoxy;

$R^{14}$ represents H or $C_{1-6}$alkyl, $C_{3-7}$cycloalkyl, $C_{3-6}$cycloalkyl$C_{1-6}$alkyl, $C_{2-6}$alkenyl, $C_{2-6}$alkynyl, phenyl or benzyl, any of which optionally bear up to 3 halogen substituents or one substituent selected from CN, $NO_2$, OH, $C_{1-4}$alkoxy, $CO_2H$, $C_{1-4}$alkoxycarbonyl, $C_{2-6}$acyl, $C_{2-6}$acyloxy, amino, $C_{1-4}$alkylamino, di($C_{1-4}$alkyl)amino, $C_{2-6}$acylamino, carbamoyl, $C_{1-4}$alkylcarbamoyl and di($C_{1-4}$alkyl)carbamoyl; and Ar represents phenyl or heteroaryl either of which optionally bears up to 3 substituents independently selected from halogen, $CF_3$, $NO_2$, CN, $OCF_3$, $C_{1-6}$alkyl and $C_{1-6}$alkoxy;

or a pharmaceutically acceptable salt thereof.

2. A compound according to claim 1 wherein X represents Ar and Ar represents optionally-substituted phenyl, pyridyl, pyrimidinyl or pyrazinyl.

3. A compound according to claim 1 wherein L is selected from $-CH_2-$, $-(CH_2)_4-$, $-(CH_2)_5-$, $-(CH_2)_2-O-(CH_2)_2-$ and $-(CH_2)_2-O-CH_2-$.

4. A compound according to claim 1 of formula II:

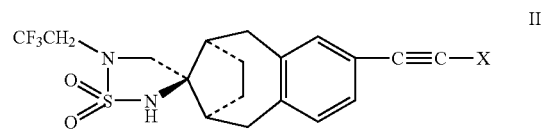

or a pharmaceutically acceptable salt thereof.

5. A compound according to claim 4 wherein X is selected from 6-membered heteroaryl, $-CH_2N(R^1)_2$, $-(CH_2)_5N(R^1)_2$, $-(CH_2)_4CON(R^1)_2$, $-(CH_2)CO_2R^2$, $-(CH_2)_2-O-CH_2CN$ and $-(CH_2)_2-O-(CH_2)_2N(R^1)_2$.

6. A compound according to claim 5 wherein X is selected from 2-pyridyl, 3-pyridyl, pyrazinyl, 4-trifluoropiperidin-1-ylmethyl, $-(CH_2)_5NH-CH_2Ph$, $-(CH_2)_4CONHCH_2Ph$, $-(CH_2)_4CO_2H$, $-(CH_2)_2-O-CH_2CN$ and $-(CH_2)_2-O-(CH_2)_2NH_2$.

7. A pharmaceutical composition comprising a compound according to any previous claim and a pharmaceutically acceptable carrier.

8. A method of treatment of a subject suffering from Alzheimer's disease which comprises administering to that person an effective amount of a compound according to any of claims 1–6.

* * * * *